(12) United States Patent
Adachi

(10) Patent No.: US 7,488,292 B2
(45) Date of Patent: Feb. 10, 2009

(54) BLOOD VESSEL DETECTION DEVICE

(75) Inventor: Hideo Adachi, Iruma (JP)

(73) Assignee: Olympus Corporation, Tokyo (JP)

( * ) Notice: Subject to any disclaimer, the term of this patent is extended or adjusted under 35 U.S.C. 154(b) by 935 days.

(21) Appl. No.: 10/872,989

(22) Filed: Jun. 21, 2004

(65) Prior Publication Data
US 2005/0033276 A1    Feb. 10, 2005

(30) Foreign Application Priority Data
Jul. 7, 2003    (JP)    ............................. 2003-193164

(51) Int. Cl.
*A61B 5/02*    (2006.01)
*A61B 17/24*   (2006.01)
*A61B 17/26*   (2006.01)
*A61B 7/00*    (2006.01)

(52) U.S. Cl. ....................... 600/504; 600/586; 600/481; 606/110; 606/113; 606/114; 606/115; 606/170

(58) Field of Classification Search ................. 600/481, 600/483, 507, 504, 586; 606/151, 157, 158, 606/110, 113, 114, 115, 170
See application file for complete search history.

(56) References Cited
U.S. PATENT DOCUMENTS
4,582,067 A    4/1986    Silverstein et al.
7,329,265 B2 *    2/2008    Burbank et al. ............. 606/157
7,344,533 B2 *    3/2008    Pearson et al. ................ 606/41
7,354,444 B2 *    4/2008    Burbank et al. ............. 606/157
7,419,487 B2 *    9/2008    Johnson et al. ............... 606/41
2002/0026188 A1 *    2/2002    Balbierz et al. ............... 606/41
2003/0120306 A1    6/2003    Burbank et al.

FOREIGN PATENT DOCUMENTS
GB    1 467 344    3/1977
JP    1-204655    8/1989
JP    06-142114   5/1994
JP    2001-309894    11/2001

* cited by examiner

*Primary Examiner*—Charles A Marmor, II
*Assistant Examiner*—Navin Natnithithadha
(74) *Attorney, Agent, or Firm*—Scully, Scott, Murphy & Presser, P.C.

(57) ABSTRACT

A blood-vessel detecting device includes a partially-deforming device which can be inserted into the body cavity so as to come into contact with the tissue surface in order to deform a part of the tissue surface so that turbulence is generated in a blood flow within blood vessels extending underneath the tissue surface, thereby enabling detection of the presence or absence of blood vessels underneath the tissue surface. Turbulent sound due to the turbulence generated at a part of the tissue surface deformed by the partially-deforming device is converted into electric signals by a converting device, following which the electric signals are subjected to signal processing such as amplification and so forth by a signal processing device.

28 Claims, 7 Drawing Sheets

FIG.1A FIG.1B
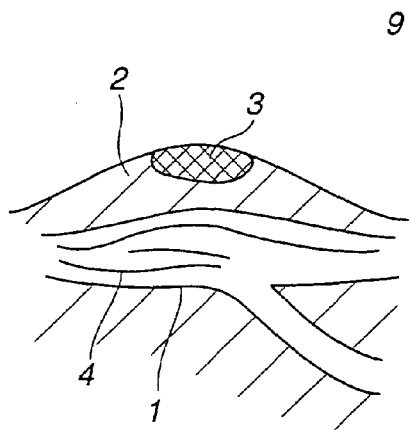
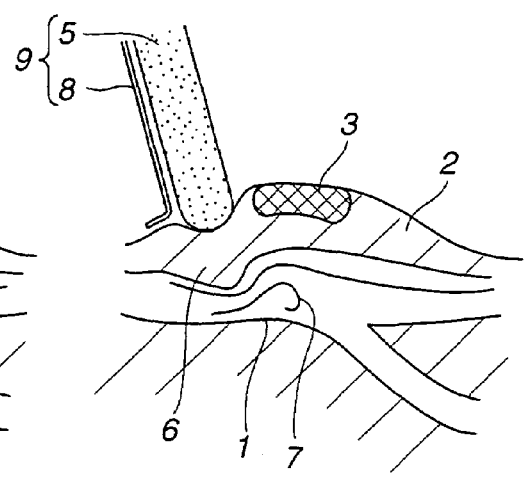
FIG.2
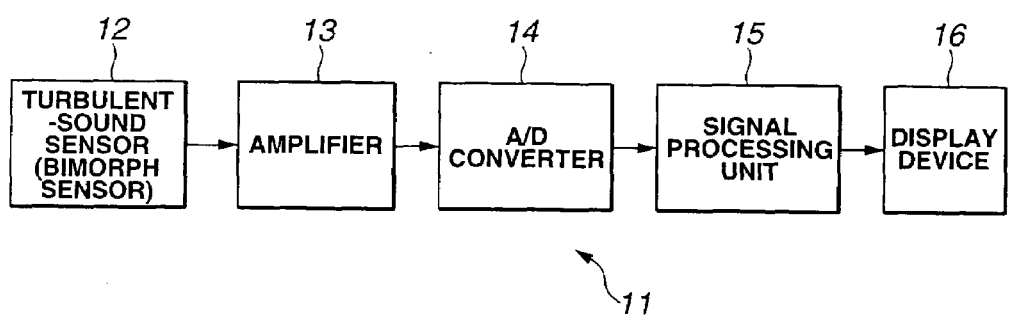

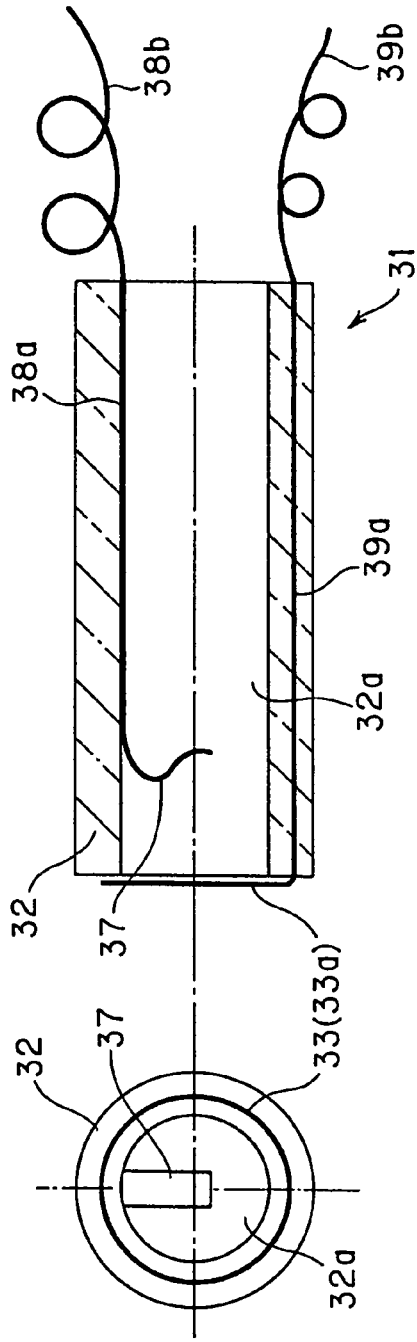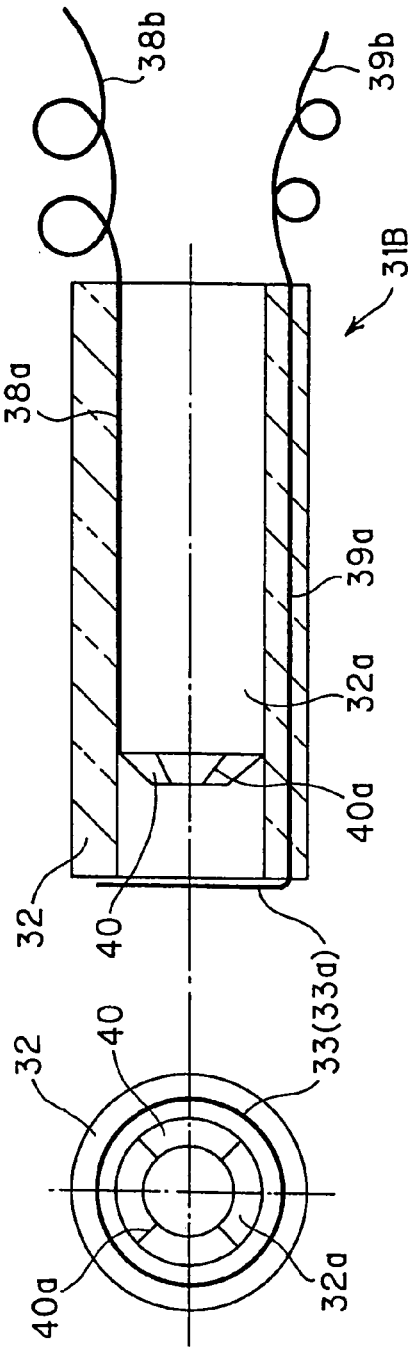

BLOOD VESSEL DETECTION DEVICE

This application claims benefit of Japanese Application No. 2003-193164 filed on Jul. 7, 2003, the contents of which are incorporated by this reference.

BACKGROUND OF THE INVENTION

1. Field of the Invention

The present invention relates to a blood vessel detecting device for detecting blood vessels around tissue, in general, which is to be resected, such as an affected portion of mucosal tissue within the body cavity.

2. Description of the Related Art

In recent years, Endoscopic Mucosal Resection (EMR) has attracted attention as a standard medical treatment for early mucosal cancer, and the clinical usefulness thereof has been well known.

In normal polypectomy, a bulging affected portion bulging therearound is resected using a high-frequency snare. On the other hand, in a case of non-bulging affected portion generally flat therearound, known resection methods include: a method wherein a tumor is caused to swell by injecting a physiological salt solution to the submucous membrane, and the tumor thus swollen is resected by a high-frequency snare; and a method wherein the affected portion is resected by the high-frequency snare while pulling up the affected portion with holding forceps using 2-channel scope; and the like.

Note that other known methods include: a method wherein the affected portion is resected by a high-frequency snare while suctioning the affected portion using a silicone tube including an endoscope and the snare inserted therethrough, (EMR tube method); a method wherein the affected portion is resected by a high-frequency snare integrally included at the tip of a transparent cap mounted at the tip of a scope while suctioning the affected portion using the transparent cap (EMRC method), a method wherein tissue around the affected portion is incised so as to resect the affected portion using an IT knife (needle knife including a ceramic chip on the tip thereof) (IT knife method).

On the other hand, in general diagnosis, blood vessels can be diagnosed by observing B-mode tomographic images or Doppler images obtained in ordinary ultrasonic endoscope diagnosis. In this case, there is the need to press an ultrasonic transducer into contact with the precise portion containing a mucous membrane which is to be resected, during transmission/reception of ultrasonic waves. Accordingly, in general, a method wherein the ultrasonic transducer is covered with a balloon filled with water is employed.

Conventionally, as another method for detecting blood vessels and aneurysms occurring in the blood vessel, a method is known wherein turbulent sound occurring in the blood vessel, i.e., Korotokov sound, is detected. The measurement of blood pressure is known as a specific application example. Description will be made regarding the technique with reference to conventional arrangements.

A sphygmomanometer disclosed in Japanese Unexamined Patent Application Publication No. 2001-309894 employs a mechanism for detecting the aforementioned-Korotokov sound.

With the aforementioned conventional sphygmomanometer, a cuff is wrapped around the upper arm of the subject, and the arteries are constricted by pressure in order to detect the Korotokov sound (K-sound). The conventional sphygmomanometer comprises a K-sound sensor for detecting the Korotokov sound (K-sound), a pressure sensor for detecting the pressure within the upper arm, a peripheral-vein pulse pressure sensor, a pressure-sensor amplifier, and the like.

In the measurement with the sphygmomanometer, the peripheral-vein pulse pressure sensor is attached onto the portion peripheral to the cuff-wrapped portion, subsequently, the peripheral-vein pulse pressure (relative value) is measured by the peripheral-vein pulse pressure sensor over the pressure of the cuff in the step of slow pressure reduction following pressure application, as well as measuring the pressure of the cuff. From the measurement results, the peak value of the peripheral-vein pulse pressure (relative value) is obtained, and the pressure of the cuff corresponding to the aforementioned peak value is determined to be the maximum peripheral-vein pulse pressure.

On the other hand, in recent research, measurement results, which suggest that cardiac murmur can be detected in a patient affected by aortopathy due to turbulence within the blood vessels thereof, have been reported as described in the document (Kanai et al. "Measurement of spatial distribution of great velocity components of the myocardium and change in thickness of the local portion thereof", J. Med. Ultrasonics, Vol. 29, No. 4, (2002) S235).

As described above, it is known that turbulence causes turbulent sound in the blood vessels, and accordingly, the blood pressure and presence or absence of an aneurysm can be detected by detecting the sound, i.e., the Korotokov sound.

SUMMARY OF THE INVENTION

A blood-vessel detection device according to the present invention for detecting the presence or absence of blood vessels underneath the tissue surface includes a partially-deforming device which can be inserted into the body cavity so as to be in contact with the tissue surface in order to deform a part of the tissue surface, thereby generating turbulence in blood passing through blood vessels extending underneath the tissue surface. Furthermore, the blood-vessel detection device includes: a converting device for converting turbulent sound due to the turbulence generated in a part of the tissue surface deformed by the partially-deforming device; and a signal processing device for performing signal processing including at least amplification for the electric signals.

BRIEF DESCRIPTION OF THE DRAWINGS

FIGS. 1A through 3 show a first embodiment according to the present invention, wherein FIG. 1A is a diagram which shows mucous tissue containing early cancer tissue, and FIG. 1B is a diagram which shows a situation wherein a blood vessel is deformed by pressing force of a pressing rod forming a blood-vessel detecting probe, leading to generation of turbulent sound;

FIG. 2 is a block diagram which shows a configuration of a signal processing device of the blood-vessel detecting device;

FIG. 3 is a block diagram which shows a detailed configuration of the signal processing device shown in FIG. 2;

FIGS. 4 through 8 show a second embodiment according to the present invention, wherein FIG. 4 is a diagram which shows a configuration, operations, and the like, of principal components according to the second embodiment of the present invention by way of an example of use;

FIG. 5A is a longitudinal cross-sectional view which shows a suction cup serving as a principal component according to the second embodiment;

FIG. 5B is a front view which shows the end face of the suction cup shown in FIG. 5A;

FIG. 6A is a longitudinal cross-sectional view which shows a suction cup serving as a principal component according to a first modification;

FIG. 6B is a front view which shows the suction cup shown in FIG. 6A;

FIG. 7 is a perspective view which shows a configuration of tip portion of the endoscope according to a second modification;

FIG. 8 is a perspective view which shows a configuration of the tip portion of the endoscope according to a third embodiment of the present invention;

FIGS. 9 and 10 show a fourth embodiment according to the present invention, wherein FIG. 9 is a diagram which shows a configuration of the tip portion of the endoscope according to the fourth embodiment by way of an example of use;

FIG. 10 is a block diagram which shows a configuration of a signal processing device;

DESCRIPTION OF THE PREFERRED EMBODIMENTS

Figure 3:
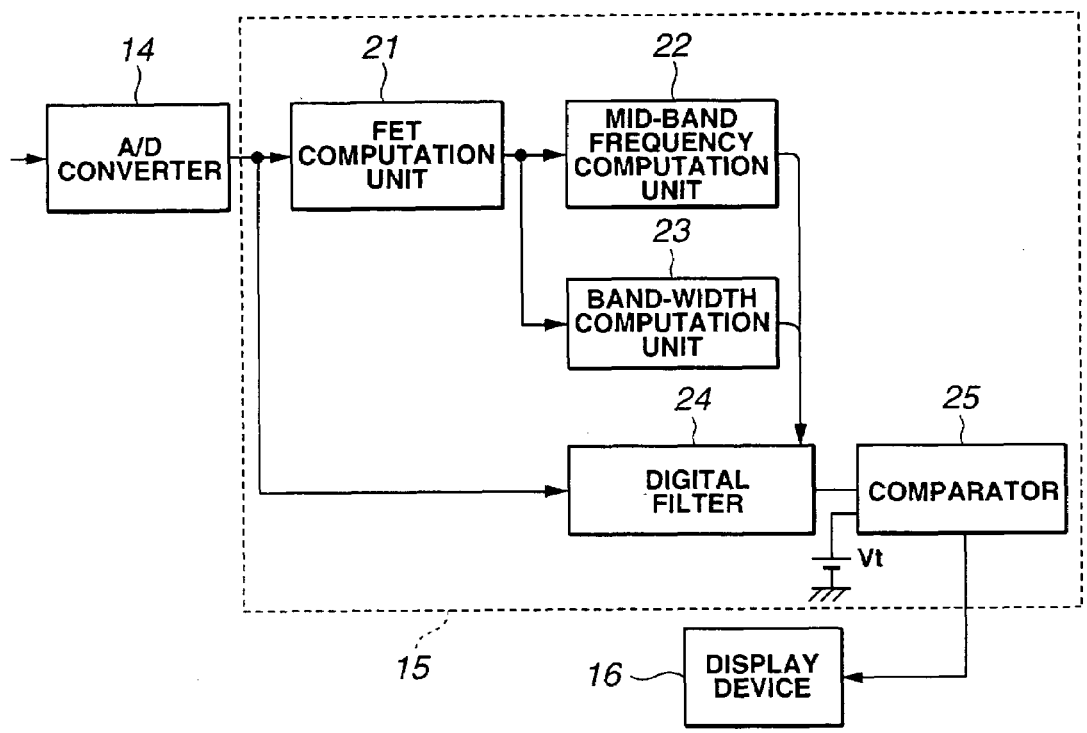

Description will be made regarding embodiments according to the present invention with reference to the drawings.

First Embodiment

Description will be made regarding a first embodiment according to the present invention with reference to FIG. 1A through FIG. 3. The present embodiment may be applied to blood vessel detection for tissue within the body cavity, and accordingly, description will be made regarding the detection for tissue within the body cavity such as mucous tissue.

In description regarding the first embodiment, first, description will be made regarding a mechanism for detecting blood vessels underneath tissue in the body cavity such as mucous tissue, following which description will be made regarding a configuration, operations, and advantages of the first embodiment.

FIG. 1A shows a blood vessel 1 underneath mucous tissue 2 containing early cancer tissue 3, and a laminar blood flow 4 passing through the blood vessel 1. Note that the laminar blood flow 4 is a generally stationary flow, and accordingly, no turbulence occurs.

In general, a fluid passing through a non-deformed tube exhibits a small Reynolds number, and accordingly, such a fluid has no turbulence. The Reynolds number Re of a viscous fluid is represented by:

$$Re = VD\rho/\eta,$$

where V denotes average fluid speed, D denotes the diameter of the tube, $\rho$ denotes the density of the fluid, and $\eta$ is viscosity of the fluid. As can be understood from the above expression, the greater the flow speed, tube diameter, or density of the fluid is, or, the smaller the viscosity of the fluid is, the greater the Reynolds number Re is, and accordingly, turbulence readily occurs.

In general, it is believed that a Reynolds number Re of 2000 or less leads to a laminar flow, and a Reynolds number Re of 3000 or more leads to a situation wherein turbulence readily occurs even in a case of a fluid passing through a non-deformed tube. In normal blood vessels without abnormal affected portions, no turbulence occurs in any normal blood vessel.

However, in blood vessels containing deposits accumulated therein, or with aneurysms therein, the blood flow passes through such a restricted portion with an extremely high blood-flow speed V as compared with other portions. In some cases, this leads to turbulence which can be detected as turbulent sound. Known medical applications employing the aforementioned mechanism include: an arrangement wherein blood pressure is measured by detecting the Korotokov sound, an arrangement wherein cerebral aneurysms are detected by detecting turbulent sound propagating through the skull (Japanese Unexamined Patent Application Publication No. 1-204655), and the like.

FIG. 1B shows the mucous tissue 2 of which a part is deformed so as to form a deformed portion 6 by pressing a long and narrow pressing rod 5, forming a blood-vessel detecting probe 9 according to the present embodiment, into contact therewith.

As described above, in a case that the blood vessel 1 exists underneath mucous tissue, pressing the blood vessel 1 deforms a part of the blood vessel 1, leading to change from the laminar blood flow 4 to a turbulent blood flow 7. The turbulent flow 7 has a flow component orthogonal to the blood vessel wall, unlike the laminar blood flow 4, leading to constriction of the blood vessel in the diameter direction, resulting in displacement of the blood vessel while vibrating.

The aforementioned displacement causes turbulent sound propagating through the mucous tissue 2, leading to vibration of the surface of the mucous tissue. The aforementioned vibration causes sound waves in a space within the body cavity. In FIG. 1B, the pressing rod 5 serves as partially-deforming means (or turbulence generating means) for deforming a part of the blood vessel 1 so as to generate turbulence.

With the blood-vessel detecting probe 9 according to the present embodiment, the pressing rod 5 integrally includes a piezo-bimorph sensor (which will be simply referred to "bimorph sensor" hereafter) 8 formed of a high-polymer piezo device for detecting blood vessels.

The bimorph sensor 8 of the blood-vessel detecting probe 9 is connected to a signal processing device 11 through an unshown signal line extending therefrom as shown in FIG. 2 so as to perform signal processing for electric signals due to turbulent sound in blood detected by the bimorph sensor 8, thereby notifying the surgeon of the presence or absence of blood vessels.

The resonance frequency fr of the bimorph sensor 8 and the output voltage Vc in a case of applying vibration force F thereto are represented by:

$$fr = (1.875^2/(43^{1/2}\pi))(t/l)(Y/\rho)^{1/2}$$

$$Vc = (3/8)g_{31}Y(l/t)^3 \Delta x$$

where t denotes the thickness of the bimorph sensor 8, l denotes the length thereof, Y denotes the Young's modulus thereof, and $\beta$ denotes the density thereof.

For example, the bimorph sensor 8 formed with Y of $2\times10^9$ [Pa], $\rho$ of $1.77\times10^3$ [kg/m$^3$], the length of 5 [mm], and the thickness of 125 [μm], exhibits resonance frequency fr of 425 [Hz].

On the other hand, in a case of the voltage output coefficient $g_{31}$ of $23\times10^{-12}$ [V/m], and the vibration displacement $\Delta x$ of 0.001 [μm], the bimorph sensor 8 generates voltage Vc of 0.005 V.

That is to say, in the event that the tissue surface vibrates with vibration displacement of 1 [nm] due to turbulent sound from the deformed blood vessel 1 in a situation wherein a part of the tissue is pressed with the small-diameter pressing rod 5 as shown in FIG. 1B, the bimorph sensor 8 outputs a voltage of 5 mV through the electrodes thereof. In other words, such an output voltage reveals presence of the blood vessel 1 underneath the mucous tissue 2 near the tip of the pressing rod 5.

Next, description will be made regarding a configuration and operations of signal processing means according to the present embodiment for performing signal processing for the output voltage Vc obtained from the electrodes of the bimorph sensor 8, with reference to the signal processing device 11 shown in FIG. 2.

The output signals from a turbulent-sound sensor 12 (more specifically, the bimorph sensor 8) are input to an amplifier 13 forming the signal processing device 11. The output signals from the amplifier 13 are converted into digital signals by an A/D converter 14. Furthermore, the digital signals are subjected to processing for extracting turbulent-sound components by a signal processing unit 15, following which the digital signals are output to a display device 16 so as to notify the surgeon of detection results for presence or absence of blood vessels.

Next, description will be made in detail regarding a configuration of the signal processing unit 15 with reference to FIG. 3.

As shown in FIG. 3, the output signals from the A/D converter 14 are divided into two, wherein one is input to an FFT computation unit 21 for performing fast Fourier transformation (which will be abbreviate to "FFT"), and the other is input to a digital filter 24. The output signals from the FFT computation unit 21 are further divided to two, wherein one is input to a mid-band frequency computation unit 22 for computing mid-band frequency from the frequency property serving as FFT computation output, and the other is input to a bandwidth computation unit 23 for computing the bandwidth thereof.

Output signals from both the computation units 22 and 23 are used as filter property setting data for the digital filter 24. Thus, the signal processing unit 15 has a configuration wherein the filter property of the digital filter 24 is determined using the data from both the computation units 22 and 23, thereby enabling efficient detection (with a high S/N ratio) of the frequency components of turbulent sound which are to be detected from the divided output signals from the A/D converter 14 while suppressing noise.

Next, description will be made regarding operations of the present embodiment.

The surgeon presses the surface of mucous tissue near the early cancer tissue 3 which is to be resected, with the pressing rod 5, so as to deform a part of the surface of the mucous tissue before resection.

Such pressing deforms the blood vessel 1, leading to generation of the turbulent flow 7, in a case that the blood vessel 1 extending underneath the mucous tissue has a diameter which is greater than that of capillaries, to the extent that a phenomenon occurs wherein in the event that the blood vessel 1 tears, blood spouts therefrom.

The turbulent blood flow 7 has momentum components orthogonal to the blood vessel wall in flow components thereof, and accordingly, the blood vessel wall vibrates, leading to vibration propagating through the mucous tissue 2 and reaching the surface of the mucous tissue, resulting in vibration on the surface of the mucous tissue.

The sound of the vibration is subjected to acoustoelectric conversion by the bimorph sensor 8, whereby electric turbulent signals are obtained. The bimorph sensor 8 is formed of a high-polymer piezo device having a high voltage-output coefficient $g_{31}$, thereby enabling highly efficient vibration-displacement/voltage conversion while suppressing the size of the bimorph sensor 8. In addition, the bimorph sensor 8 having such a configuration has a wide frequency band property, thereby enabling efficient detection of turbulent sound from blood vessels with various diameters.

Furthermore, the aforementioned high-polymer piezo device is formed of a flexible material containing fluorine which exhibits marked stability from the chemical perspective, thereby enabling smooth contact of the bimorph sensor 8 with the surface of tissue, and thereby preventing deterioration in the performance thereof due to material deterioration thereof.

The turbulent-sound signals converted into electric signals by the bimorph sensor 8 are amplified by the amplifier 13 shown in FIG. 2, following which the electric signals are converted into digital signals by the A/D converter 14, which can be subjected to high-speed computation using various types of calculation algorithms.

In general, the turbulent-sound signals contain various noise components. The signal processing unit 15 performs processing for the turbulent-sound signals in order to remove the noise components therefrom.

First, the frequency property of the turbulent-sound signals is computed with frequency analysis processing performed in the FFT computation unit 21. That is to say, the FFT computation unit 21 computes the mid-band frequency taken as a feature value of the frequency property of the turbulent-sound signals; the −6 dB upper-side cutoff frequency which is lower than that of the mid-band frequency by a predetermined decibel, specifically lower by 6 dB; the −6 dB lower-side cutoff frequency which is lower than that of the mid-band frequency by −6 dB; and the frequency passing bandwidth between the lower- and upper-side frequencies of −6 dB of the mid-band frequency; and the like.

Note that description has been made regarding an arrangement wherein the bandwidth is determined to be a specific width between the lower- and upper-side cutoff frequencies of −6 dB of the mid-band frequency, arrangements may be made wherein the bandwidth is determined to be a width therebetween of −20 dB and so forth.

Subsequently, the user designs the digital filter 24 so as to have generally the same band property as with the turbulent sound signals using the frequency analysis processing results obtained by the FFT computation unit 21. The digital filter 24 processes the aforementioned amplified turbulent sound signals so as to efficiently remove the noise components having frequency components different from those of the turbulent sound signals.

Thus, processing by the signal processing unit 15 realizes high S/N turbulent sound signals, thereby enabling detection of presence or absence of blood vessels underneath mucous tissue, having a relatively large diameter with a high S/N ratio by confirming presence or absence of the aforementioned turbulent sound signals.

In this case, a comparator 25 makes a comparison between: the signals of the processed results from the signal processing unit 15; and a predetermined threshold Vt or the like serving as a reference value, and the comparison results are output on the display device 16, for example, thereby notifying the surgeon or the like, of the presence or absence of blood vessels extending underneath the mucous tissue which is to be resected prior to performing the EMR method.

As described above, with the present embodiment, the surgeon or the like is notified of presence or absence of blood vessels extending underneath the mucous tissue prior to performing EMR method, thereby preventing unexpected bleeding. Thus, in a case of resection of an affected portion such as the early cancer tissue 3 or the like which is to be resected, the surgeon can easily confirm presence or absence of the blood vessel 1 extending underneath (within) the portion which is to be resected, using the blood vessel detecting device according to the present embodiment, thereby greatly reducing the load of the surgeon in such a case.

While description has not been made regarding any specific configuration of resecting means with reference to the drawings in the present embodiment, specific description thereof will be made regarding the configuration thereof and the like in the following embodiment. Note that in a case that the aforementioned pressing rod 5 or the like is used under observation with an endoscope, the rod 5 or the like is formed with a diameter small enough to be inserted into an channel of the endoscope as described later.

Second Embodiment

Next, description will be made regarding a second embodiment with reference to FIGS. 4 through 7. Note that in the present embodiment, description will be omitted regarding configurations which are the same as with the first embodiment.

Figure 4:
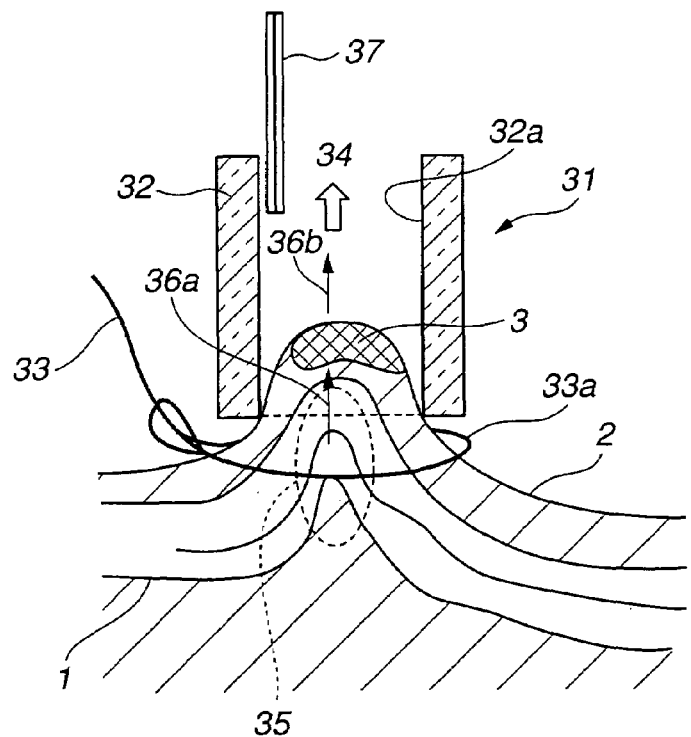

FIG. 4 shows principal components forming a mucous-tissue resection device 31 according to a second embodiment serving as a tissue resection device according to the present invention, suitable for resection of mucous tissue within the body cavity.

FIG. 4 is a schematic diagram which shows a technique wherein a part of the mucous tissue 2 containing the early cancer tissue 3 is suctioned with a transparent and cylindrical suction cup 32 mounted at the tip of an unshown endoscope, a loop portion (ring portion) 33a of a high-frequency snare 33 is put on the neck of the mucous tissue protruding due to the aforementioned suctioning so as to be resected by cauterizing.

Note that the endoscope has a configuration wherein channels are opened at the tip thereof for mounting the suction cup, the base of the channels are connected to a suction pump or the like, and suctioning force can be applied to the space within the suction cap by suctioning actions of the suction pump, as described later with reference to FIG. 7.

In the event that the blood vessel 1 extends underneath the mucous tissue 2 containing the early cancer tissue 3 protruding due to suctioning force 34 (denoted by an outline arrow in FIG. 4) within the suction cup 32, the blood vessel 1 is deformed, as well, leading to formation of a deformed portion 35 underneath the mucous tissue. In the event that the blood vessel contained in the deformed portion 35 exists at a position which is to be resected by cauterizing with the high-frequency snare 33, resection thereof leads to a large amount of bleeding.

On the other hand, a turbulent flow occurs in the blood vessel within the deformed portion 35, leading to turbulent sound 36a propagating through the blood vessel wall up to the surface of the mucous tissue so as to vibrate the surface of the mucous tissue, resulting in radiation sound 36b in a hollow portion 32a of the suction cup 32.

With the present embodiment, the radiation sound 36b is detected by a bimorph sensor 37 formed of a high-sensitivity high-polymer piezo device, of which the tip is disposed within the hollow portion 32a. That is to say, the radiation sound vibrates the bimorph sensor 37 within the hollow portion 32a, and the bimorph sensor 37 converts the vibration into electric turbulent sound signals.

The mucous-tissue resection device 31 according to the present embodiment features a configuration wherein the bimorph sensor 37 is not directly in contact with the surface of the mucous tissue, but the bimorph sensor 37 is disposed at a position within the hollow portion 32a, distanced from the surface of the mucous tissue for detecting sound.

Vibration generated on the surface of the mucous tissue may contain the frequency components parallel to the direction along the surface of the mucous tissue which has no relation with the turbulent sound, as well as the frequency components orthogonal to the surface of the mucous tissue, i.e., the frequency components due to displacement of the surface of the mucous tissue in the direction orthogonal thereto due to the turbulent sound. The contact-type sensor for detecting turbulent sound has the disadvantage of detecting both vibration components, leading to great deterioration in the S/N ratio.

With the present embodiment, the bimorph sensor 37 selectively detects only the frequency components orthogonal to the surface of the mucous tissue which can propagate through space, thereby realizing detection of turbulent sound with an excellent S/N ratio. On the other hand, with a configuration wherein such a sensor is disposed within the body cavity in an ordinary situation without any means for preventing sound generated in other portions, the sensor detects sound generated in all the portions within the body cavity.

However, The mucous-tissue resection device 31 according to the present embodiment has a configuration wherein the bimorph sensor 37 is disposed within the suction cup 32 serving as the closed hollow portion 32a, thereby almost completely preventing sound propagating from the other portions within the body cavity, and thereby enabling detection of turbulent sound with an excellent S/N ratio, i.e., detecting presence or absence of blood vessels in the deformed portion 35 in a sure manner.

The bimorph sensor 37 shown in FIG. 4 is formed in the shape of a rectangle, and more specifically, has a configuration as shown in FIGS. 5A and 5B. FIG. 5A is a longitudinal cross-sectional view which shows the suction cup 32, and FIG. 5B is a front view which shows the end face thereof.

As shown in FIGS. 5A and 5B, the suction cup 32 integrally includes the high-frequency snare 33 (the loop 33a thereof) at the end (tip) for contact with the mucous tissue 2, and accordingly, the early cancer tissue 3 is resected by cauterizing a region with the same diameter as with the suction cup 32.

The mucous-tissue resection device 31 according to the present embodiment has a configuration wherein the rectangular bimorph sensor 37 is disposed at a position so as not to directly come in contact with the surface of the mucous tissue during suctioning, and the detected turbulent sound signals are output through a line 38a disposed along or near the inner wall of the suction cup 32 and a cable 38b extending from rear base of the suction cup 32.

On the other hand, high-frequency signals are supplied to the high-frequency snare 33 through a wire 39a embedded within the inner wall of the suction cup 32 or the like, and a wire 39b extending from the rear end of the suction cup 32.

FIGS. 6A and 6B show a principal portion of a mucous-tissue resection device 31B serving as a modification of the present embodiment. With the modification, a ring-shape bimorph sensor 40 is employed for detecting turbulent sound, instead of the rectangular bimorph sensor 37 shown in FIGS. 5A and 5B.

The bimorph sensor 40 is formed in the shape of a ring, and includes notches 40a so as to be readily bent and deformed. Note that the mucous-tissue resection device 31B has the same configuration as with the arrangement shown in FIGS. 5A and 5B, except for the configuration of the bimorph sensor.

Both the bimorph sensors 37 and 40, each of which are formed of a high-polymer piezo device, have a configuration so as not to inhibit suctioning.

Figure 7:
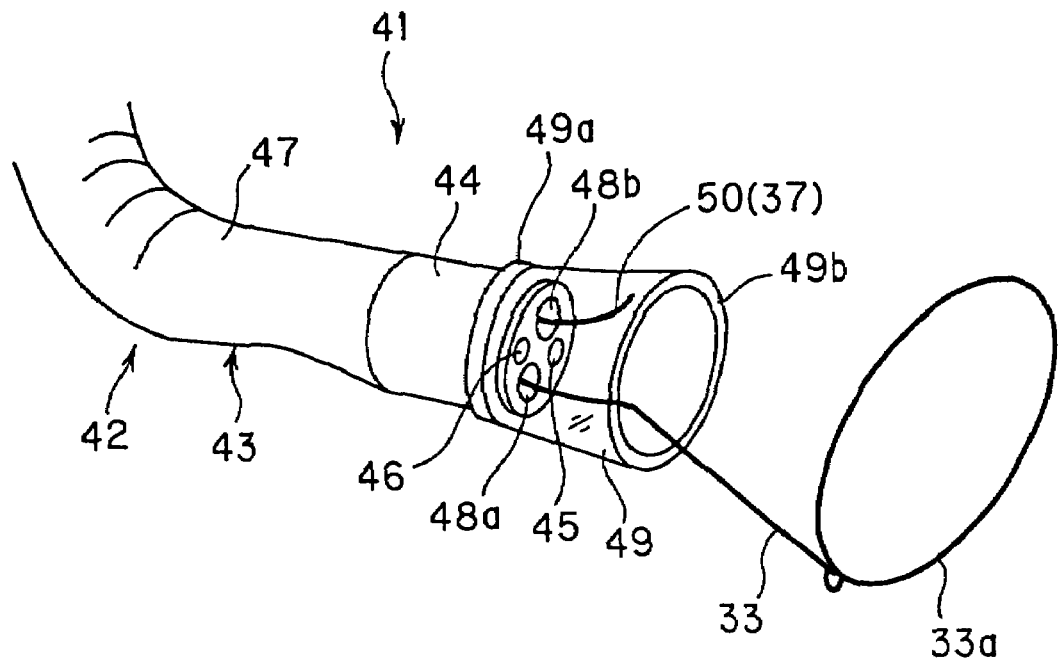

FIG. 7 shows a mucous-tissue resection device 41 serving as another modification of the present invention having a configuration wherein the transparent-cup EMRC method includes a turbulent sound detecting function.

The mucous-tissue resection device 41 includes an narrow and long inserting portion 43 of an endoscope 42 which can be inserted into the body cavity, and a rigid tip 44 formed at the tip of the inserting portion 43 includes an observation window 45 having an objective optical system which allows the surgeon to perform optical observation, and an illumination window 46 (for casting illumination during observation), at the tip thereof.

The objective optical system includes the end face of an image guide for transmitting optical images, or an image pickup face of a solid state image pickup device such as a charge coupled device (which will be abbreviated to "CCD") at the focusing position thereof. On the other hand, the illumination window includes the end face of a light guide for transmitting illumination light, wherein the illumination light cast (from a light source device) to the base face of the light guide is transmitted through the light guide, and is output from the end face, whereby the region which is to be observed through the observation window 45 is illuminated.

With an optical endoscope including an image guide of which the end face is disposed at the observation window 45 thereof, the user can observe optical images transmitted to the rear end face of the image guide through an eyepiece unit.

On the other hand, with an electronic endoscope including a solid state image pickup device, the solid state image pickup device is connected to a video processor serving as a video signal processing device through a signal line, the image signals subjected to photoelectric conversion by the solid state image pickup device are converted into video signals by the video processor so as to be output to an image display device such as a monitor or the like, whereby an image focused on the image pickup face of the solid state image pickup device is displayed on a display screen of the image display device.

Furthermore, the endoscope 42 includes a curving portion 47 curvably disposed at the base end of the tip 44 of thereof, wherein the user can curve the curving portion 47 in a desired direction by operating a curving knob disposed on an unshown operation unit disposed at the base end of the inserting portion 43, whereby the user can control the tip 44 so as to face a desired direction.

That is to say, with the mucous-tissue resection device 41 according to the present embodiment, the user can control the tip 44 such that mucous tissue which is to be resected (containing the early cancer tissue 3) comes into the field of view of the observation window 45 disposed at the tip 44 by controlling the curving portion 47, and furthermore, medical treatment such as resection or the like can be made while observing the mucous tissue through the endoscope 42.

Furthermore, the inserting portion 43 includes multiple channels for inserting forceps or the like along the longitudinal direction thereof, for example, wherein the channels lead to channel openings (which will be also referred to as "forceps opening") 48a and 48b formed on the end face of the tip 44.

The inserting portion 43 includes inserting openings around the base end thereof, each of which communicate with the corresponding channel for inserting forceps or the like. In this case, each channel forks into two near the inserting opening, wherein one extends to the operation unit, and the other communicates with a suctioning tube which is inserted into a universal cord extending on the side of the operation unit through the suctioning operation unit of the operation unit.

In this case, the user connects a connector disposed at the end of the universal cord to the light source device, whereby the cap of the suctioning tube is connected to a suctioning pump disposed within the light source device. Thus, the user can perform suctioning by operating the suctioning operation unit, through the forceps openings 48a and 48b formed on the tip 44, which lead to the channels communicating with the suctioning tube.

The mucous-tissue resection device 41 according to the present embodiment has a configuration wherein a transparent cup 49 is mounted onto the tip 44 with the base end thereof, and the high-frequency snare 33 extends from one forceps opening 48a for resection, as well as a turbulent sound sensor 50, e.g., the bimorph sensor 37, extending from the other forceps opening 48b.

Note that the mucous-tissue resection device 41 according to the present embodiment includes two forceps openings 48a and 48b, and accordingly, an arrangement may be made wherein only one forceps opening 48b communicates with the suctioning tube, for example.

Note that a commercially-available transparent cup may be employed as the transparent cup 49. More specifically, the transparent cup 49 includes a cylindrical main body formed of polycarbonate or the like, and an endoscope mounting portion 49a formed of polyvinyl chloride or the like, at the base end of the main body for mounting the tip 44 of the endoscope 42, which is fixed by adhesion or the like.

The cable from the base end of the high-frequency snare 33 extends outside of the endoscope 42 through the inserting opening of the channel, and is connected to an unshown high-frequency power supply device for supplying high frequency current. Upon the user turning on a foot switch or the like, the high-frequency power supply device supplies a high-frequency current to the high-frequency snare 33 so as to cauterize and resect a portion surrounded by the loop portion 33a of the high-frequency snare 33.

On the other hand, the cable from the turbulent sound sensor 50 (bimorph sensor 37) protruding from the forceps opening 48b extends outside of the endoscope 42 through the inserting opening of the channel, and is connected to the signal processing device 11 or the like shown in FIG. 2.

As described above, the mucous-tissue resection device 41 according to the present embodiment has a function serving as a resection device for performing resection of a portion which is to be resected such as mucous tissue containing early cancer tissue or the like while observing through the endoscope 42, i.e., while observing the mucous tissue through the observation window 45 using illumination through the illumination window 46, and has a function wherein the surgeon can diagnose presence or absence of blood vessels extending underneath (within) the portion which is to be resected prior to resection thereof using the turbulent sound sensor 50.

With the present embodiment, at the time of medical treatment such as resection of early cancer tissue, the surgeon adjusts the loop portion 33a of the high-frequency snare 33 such that the diameter thereof is generally the same as the inner diameter of the cylindrical transparent cup 49. Subsequently, the surgeon controls the tip 49b of the transparent cup 49 such that the high-frequency snare 33 comes into contact with the early cancer tissue so as to encompass it, whereby the early cancer tissue is sealed in a generally closed space.

Subsequently, upon the surgeon operating the suctioning operation unit (specifically, the suctioning button) of the endoscope 42 in order to start suctioning, the surface of the mucous tissue containing the early cancer tissue begins to bulge upwards due to suctioning force in the generally closed space. Thus, the suction cup 49 (and suctioning means) has a function serving as means for deforming a part of tissue.

Such a configuration according to the present embodiment has the advantage that the surgeon can control the tip position of the bimorph sensor 37 by operating the operation unit of the endoscope 42, and can control the tip portion thereof so as to exhibit optimal contact state for detection of turbulent sound while observing detection signals.

Furthermore, such a configuration according to the present embodiment has the advantage that a commercially-available suction cup may be employed as the suction cup 49 without modification. Note that with the suction cup 32 shown in FIG. 4, a commercially-available suction cup may be employed, as well.

With the above-described embodiment (and modifications thereof), the mucous tissue containing the early cancer tissue which is to be resected is suctioned so as to protrude using the suction cup 32 or 49, and in the event that blood vessels having a relatively large diameter extends underneath the mucous tissue, the blood vessels contained in the portion which is to be resected by cauterizing using the high-frequency snare 33 are greatly deformed, leading to generation of turbulent sound.

The turbulent sound is emitted as sound waves from the surface of the mucous tissue over a space within the body cavity. With the present embodiment, the bimorph sensor 37 integrally included within the suction cup 32 or 49 detects the sound waves, thereby enabling determination whether or not blood vessels having a relatively large diameter extend underneath the mucous tissue.

Sound components generated within the body cavity contain various frequency components due to various kinds of actions such as breathing, which have no relation with the aforementioned turbulent sound, leading to noise at the time of detection of turbulent sound. However, with the present embodiment, the bimorph sensor 37 is disposed within the suction cup 32 or 49 so as to prevent such noise, thereby enabling detection of turbulent sound with an excellent S/N ratio.

As described above, with the present embodiment, the high-frequency snare 33 includes a blood vessel detection diagnostic probe near the resection means thereof for detecting the presence or absence of blood vessels extending underneath mucous tissue, and accordingly, the surgeon can diagnose whether or not blood vessels extend around the portion which is to be resected prior to resection, thereby facilitating suitable medical treatment.

Third Embodiment

Next, description will be made regarding a third embodiment according to the present invention with reference to FIG. 8. Note that in the present embodiment, description of configurations which are the same as with the first or second embodiments will be omitted or will be made in brief.

The mucous-tissue resection device 51 according to the present embodiment has the same configuration as with the second embodiment, wherein an endoscope-mounting portion 52a disposed at the base end of a suctioning cup 52 is connected to the tip 44 of the endoscope 42, whereby the suction cup 52 is mounted onto the endoscope 42.

The suction cup 52 is formed with a greater length than that of the suction cup 49 according to the second embodiment, and has a configuration wherein a resonant tube 53 is disposed at a position over the range between: the generally middle portion of the suction cup 52 along the longitudinal direction thereof; and the base end thereof, and the resonant tube 53 includes a sound-wave microphone 54 in the shape of a membrane.

That is to say, the difference in the present embodiment from the second embodiment is that the suction cup 52 includes two parts, wherein one is a front portion 52b generally corresponding to the suction cup 49 according to the second embodiment, and the other is a rear portion 52c serving as the base end thereof.

Furthermore, the front portion 52b of the suction cup 52 includes the resonant tube 53 extending from the forceps opening 48b formed on the base end thereof positioned generally at the connecting portion between both the portion 52b and 52c, and the resonant tube 53 includes the sound-wave microphone 54 in the shape of a membrane. Note that reference numeral 53a in FIG. 8 denotes an opening formed at the tip of the resonant tube 53.

Note that the sound-wave microphone 54 according to the present embodiment is not restricted to a piezo microphone using the piezo effect, rather, an arrangement may be made wherein an electrostatic microphone using the electrostatic effect is employed as the sound-wave microphone 54.

With such an arrangement employing an electrostatic microphone as the sound-wave microphone 54, sound waves can be handled over a wider bandwidth than with an arrangement employing a piezo microphone, thereby enabling detection of turbulent sound singles in a wide frequency range. Note that the mucous-tissue resection device 51 according to the present embodiment has the same configuration as with the second embodiment, except for the aforementioned configuration.

Next, description will be made regarding operations of the present embodiment.

The surgeon connects an unshown microphone line to the sound-wave microphone 54 extending up to the tip 44 of the endoscope 42 through the forceps opening 48b, following which the surgeon mounts the transparent suction cup 52 formed of the front and rear portions 52b and 52c onto the tip 44 of the endoscope 42 such that the field of view of the observation window 45 and the illumination window 46 are not obstructed.

Subsequently, the surgeon adjusts the loop portion 33a of the high-frequency snare 33 extending outside of the tip 44 through the forceps opening 48a such that the diameter thereof is suitable for surrounding the early cancer tissue, following which the surgeon controls the tip 52d of the suction cup 52 such that both the tip 52d and the loop portion 33a come in contact with the mucous tissue containing the early cancer tissue. Subsequently, the surgeon performs suctioning of the mucous tissue through the suction cup 52 so as to form a protrusion.

In this situation, in the event that there are any blood vessels extending underneath the protruding mucous tissue, the blood vessels contained therein are greatly deformed, leading to generation of turbulent sound. The turbulent sound reaches the microphone 54 through the resonant tube 53, following which the acoustic vibrations are converted into the electric signals by the microphone 54.

The turbulent sound signals, which are converted electric signals, are subjected to signal processing by the signal processing device 11 described in the first embodiment. Upon detection of signals which reveals presence of the blood vessel 1 extending underneath the mucous tissue, the detection results thereof are displayed on the display device 16, thereby notifying the surgeon that the surgeon should stop resection with the high-frequency snare 33.

As described above, the mucous-tissue resection device 51 according to the present embodiment has a configuration wherein the signal level of the turbulent sound is increased by the resonant tube 53, and the sound generated in the body cavity other than the turbulent sound is interrupted by the suction cup 52, thereby improving the S/N ratio of signal detection of turbulent sound. Thus, the mucous-tissue resection device 51 according to the present embodiment detects blood vessels extending underneath mucous tissue with an excellent S/N ratio.

Fourth Embodiment

Next, description will be made regarding a fourth embodiment with reference to FIGS. 9 through 10. Note that in the present embodiment, description of configurations the same as with the first through third embodiments will be omitted or will be made in brief.

Figure 8:
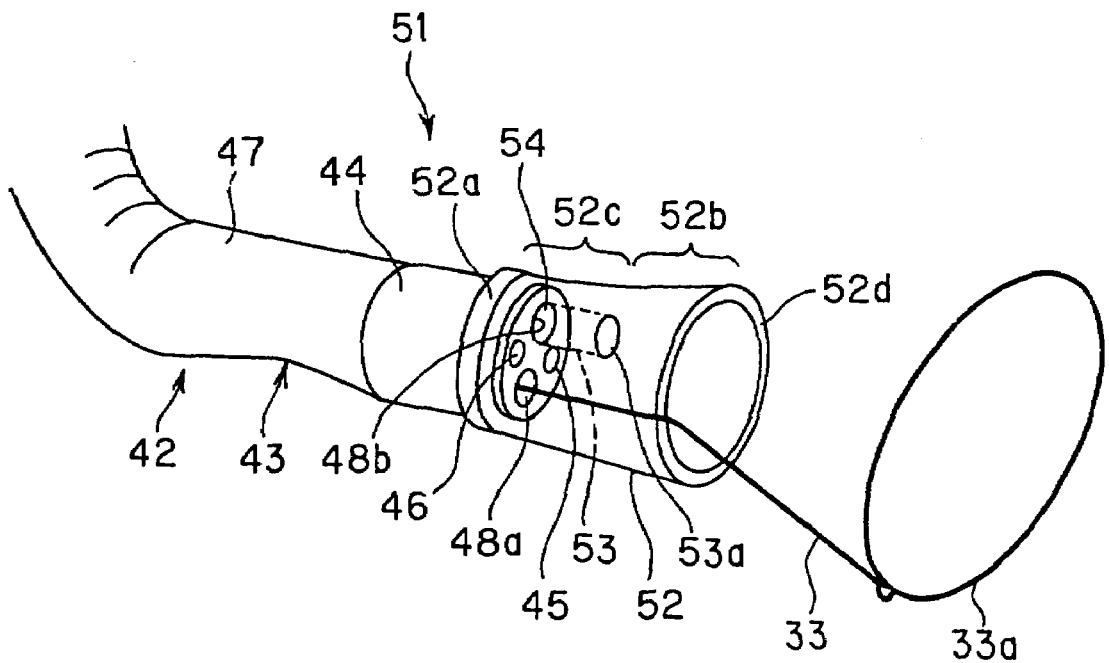
Figure 9:
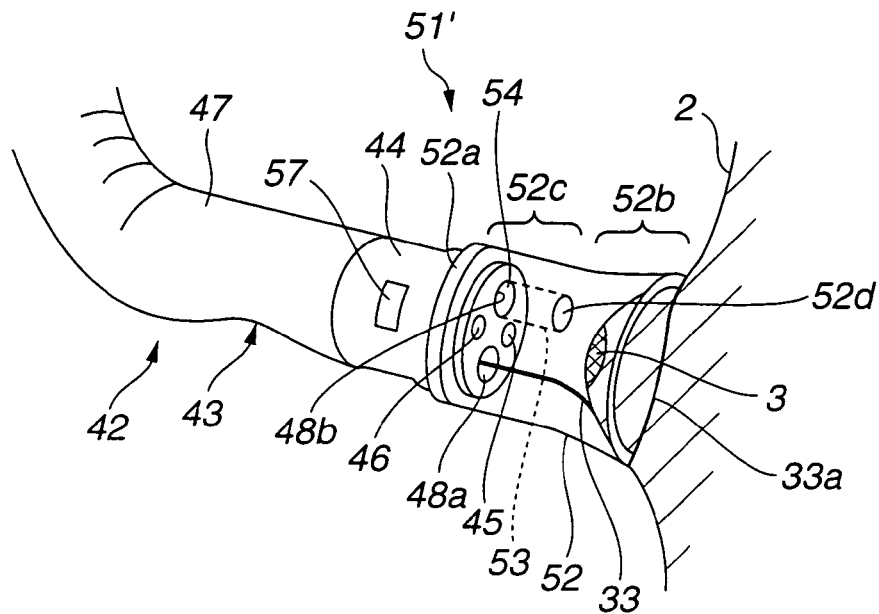

A mucous-tissue resection device 51' according to the fourth embodiment shown in FIG. 9 has basically the same configuration as with the mucous-tissue resection device 51 according to the third embodiment shown in FIG. 8, except for a configuration wherein the endoscope 42 further includes a background noise sensor 57.

That is to say, the mucous-tissue resection device 51' includes the background noise sensor 57 on the outer face of the tip 44 (for mounting the suction cup 52) of the endoscope 42 for detecting background noise.

The detection signals detected by the background noise sensor 57 are input to a signal processing device 58, described later with-reference to FIG. 10, through an unshown signal line.

In the present embodiment, description will be made regarding the mucous-tissue resection device 51' in a situation wherein the surgeon determines presence or absence of blood vessels extending underneath the mucous tissue prior to medical treatment of the early cancer tissue 3.

In this case, the mucous tissue 2 containing the early cancer tissue 3 therein is suctioned through the suction cup 52 so as to form a protrusion, and at the same time, the loop portion 33a of the high-frequency snare 33 comes into contact with the mucous tissue 2 so as to surround the base portion of the protrusion thereof. In this situation, upon the surgeon applies a high-frequency current to the high-frequency snare 33, the mucous tissue 2 surrounded by the loop portion 33a is resected.

In general, sound components generated from the surface of mucous tissue contain various frequency components including noise components in the body cavity other than turbulent sound signals.

In many cases, the noise in the body cavity is generated due to beating of the heart, and accordingly, such noise has a constant cycle period, i.e., a constant cycle frequency. In many cases, the turbulent sound signals detected by the microphone 54 are superimposed on such noise signals generated in the body cavity.

Accordingly, with the present embodiment, pure noise signals in the body cavity which contain no turbulent sound signals are detected from the turbulent sound signals containing the noise signals in the body cavity superimposed thereon, and the pure noise signals in the body cavity are subtracted from the turbulent sound signals containing the noise signals in the body cavity superimposed thereon, whereby pure turbulent sound signals are obtained.

A configuration wherein the background noise sensor 57 is disposed within the suction cup 52 has difficulty in detecting such pure noise signals in the body cavity. Accordingly, the mucous-tissue resection device 51' according to the present embodiment has a configuration wherein the background noise sensor 57 is disposed at a position near the suction cup 52 and outside thereof for detecting the noise in the body cavity as shown in FIG. 9.

Figure 10:
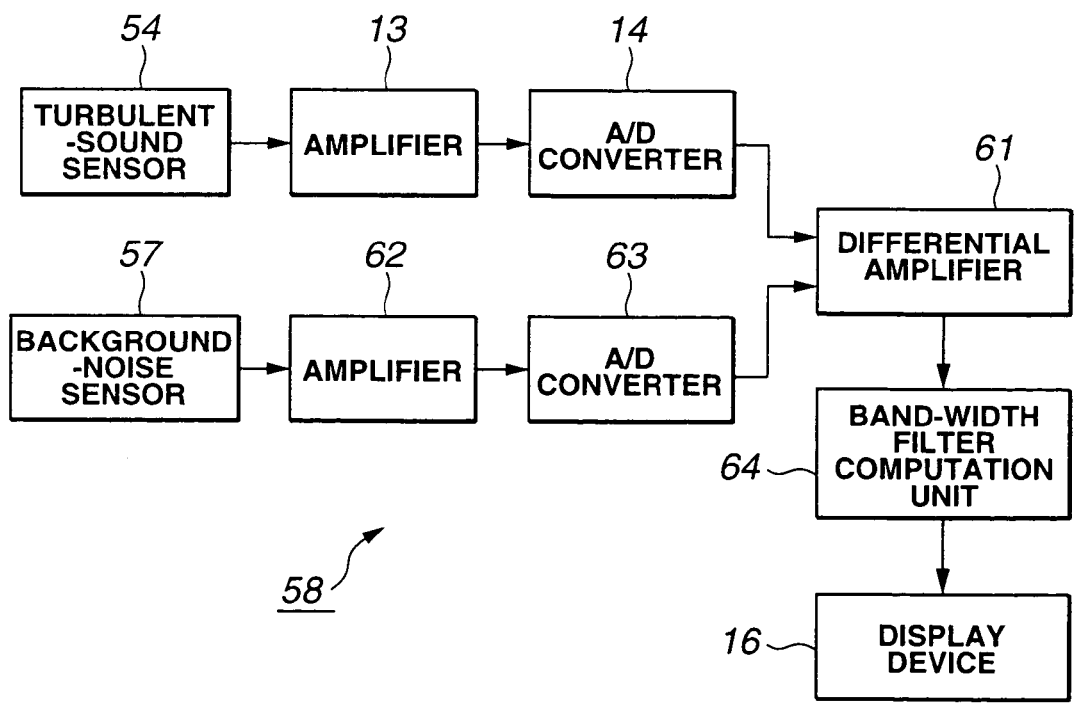

FIG. 10 shows a configuration of the signal processing device 58 for performing signal processing for detection signals from the turbulent sound sensor 54 and the background noise sensor 57 so as to determine presence or absence of blood vessels extending underneath mucous tissue with high precision.

The detection signals from the turbulent sound sensor 54 are input to one of input terminals of a differential computation unit 61 through the amplifier 13 and the A/D converter 14. On the other hand, the detection signals from the background noise sensor 57 are input to the other input terminal of the differential computation unit 61 through an amplifier 62 and an A/D converter 63 in the same way.

The differential computation unit 61 computes differential signal between both the detection signals, following which the differential signal thus obtained is subjected to filter processing by a bandwidth filter computation unit 64. Furthermore, the bandwidth filter computation unit 64 determines whether or not the received differential signal exceeds a predetermined threshold, and in the event that determination has been made that the differential signal exceeds the predetermined threshold, the output signals are transmitted to the display device 16 in order to output notification signals.

The mucous-tissue resection device 51' according to the present embodiment has advantages described below.

In the event that the mucous tissue protruding by actions of such a configuration according to the present embodiment contains blood vessels with a relatively great diameter, to the extent that a phenomenon occurs wherein in the event that the blood vessel 1 tears, blood spouts therefrom, such blood vessels are greatly deformed due to protrusion of the mucous tissue, leading to generation of turbulent sound.

The sound waves thus generated are detected by the microphone 54 disposed within the suction cup 52, as well as detecting the background noise by the microphone 57 disposed outside of the suction cup 52, and differential output therebetween is obtained, thereby realizing detection of turbulent sound subjected to removal of noise due to beating of the heart, and thereby enabling detection of turbulent sound with high precision, i.e., with a high S/N ratio.

With the present embodiment, determination of the presence or absence of blood vessels underneath mucous tissue can be made with high precision, thereby preventing unexpected bleeding in the patient due to resection during Endoscopic Mucosal Resection (EMR), and thereby improving QOL (Quality of Life) of the patient.

Fifth Embodiment

Next, description will be made regarding a fifth embodiment according to the present invention with reference to FIG. 11.

Figure 11:
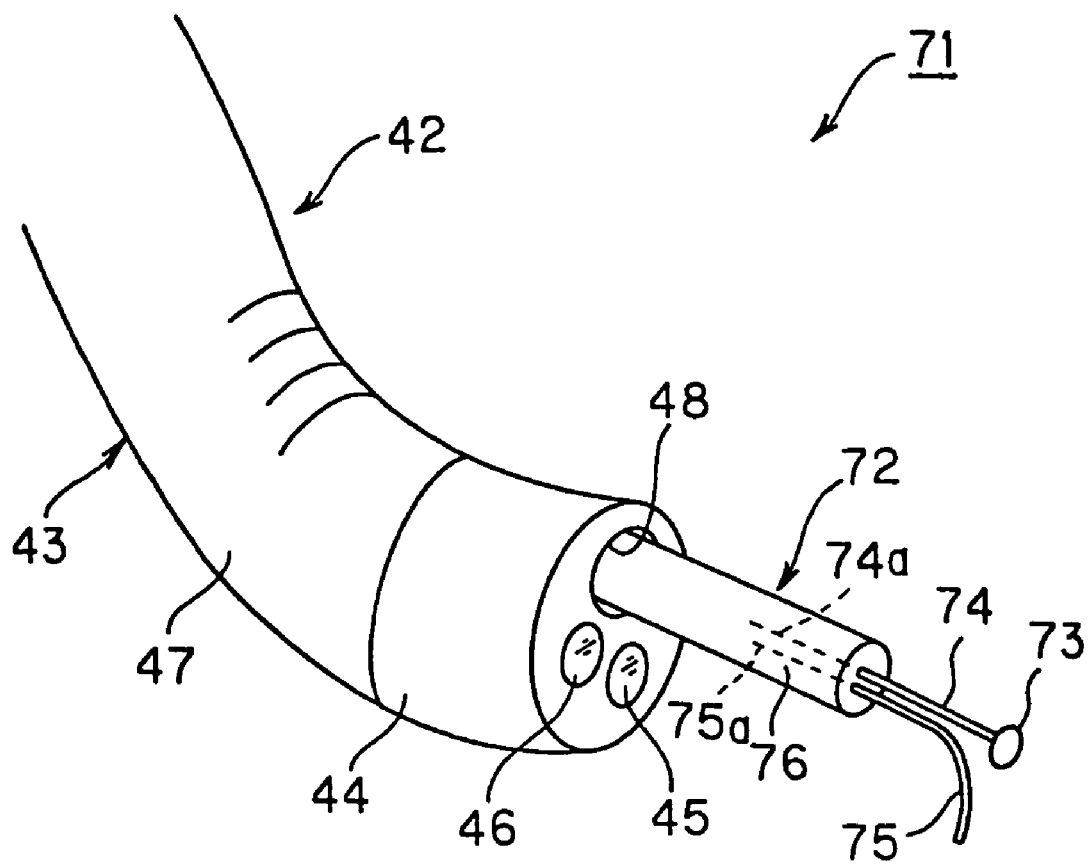
FIG. 11 is a diagram which shows a configuration of the tip portion of the endoscope according to a fifth embodiment of the present invention.

FIG. 11 shows a mucous-tissue resection device 71 according to the present embodiment in a situation immediately prior to resection.

That is to say, FIG. 11 shows the mucous-tissue resection device 71 having an IT knife 72 serving as a needle knife integrally including a turbulent-sound detection vibration sensor and a ceramic chip serving as mucous-tissue resecting means, in a situation wherein the tip of the IT knife 72 is extracted from the forceps opening 48 formed on the endoscope 42 immediately prior to resection while optically observing mucous tissue through the observation window 45 of the endoscope 42.

Note that the endoscope 42 according to the present embodiment may include only a single forceps opening 48.

The aforementioned IT knife 72 integrally including the turbulent-sound detection vibration sensor comprises: a metal needle portion (needle portion) 74 including a ceramic ball 73 at the tip thereof; a curving displacement sensor chip 75 formed of a high-polymer piezo bimorph sensor in the shape of a rectangle, for example, for detecting small vibration; and a small-diameter rod 76 for fixedly supporting the IT knife 72 and the curving displacement sensor chip 75 so as to protrude from the end face thereof.

The small-diameter rod 76 for supporting the bases of the needle portion 74 and the curving displacement sensor chip 75 protruding therefrom along the axial direction includes: a line 74a for supplying high-frequency electric power to the needle portion 74; and a line 75a for transmitting detection signals from the curving displacement sensor chip 75, contained therewithin.

Next, description will be made regarding operations of the present embodiment.

While the suctioning cup method described above has the disadvantage that only tumor tissue with a size within that of the cup can be resected, the IT knife method is an EMR method having the advantage of enabling resection of tissue with a diameter of 2 cm or more without remaining tumor tissue using the IT knife serving as treatment means for resecting a malignant tumor such as early cancer tissue.

In medical treatment according to the IT knife method, first, the surgeon marks a line for incising, so as to surround the tumor, further out from the perimeter of the tumor by around 4 mm, using the tip of the IT knife 72.

Subsequently, the surgeon injects a sodium-hyaluronate solution or the like underneath mucous tissue at a portion on the perimeter of the tumor in order to bulge the mucous tissue which is to be resected, surrounded by the aforementioned line. Furthermore, the surgeon incises the mucous tissue which is to be resected along the marked line with the IT knife 72, whereby the mucous tissue is incised along the line surrounding the tumor.

Subsequently, the surgeon injects a physiological salt solution underneath the middle portion of the tumor in order to separate the entire tumor from the muscle layer, following which the surgeon performs snaring wherein the tip of the snare is pressed into contact with the groove formed by the aforementioned incision around the perimeter of the tumor so as to expand the groove for resection of the tumor, whereby resection of the tumor tissue is completed.

In such a technique, in general, the needle portion 74 includes the ceramic ball 73 at the tip thereof for facilitating resection. However, in the event that there are blood vessels with a relatively great diameter underneath mucous tissue, the ceramic ball 73 may be caught on the blood vessel, and accordingly, the needle portion 74 may snag the blood vessel.

In this case, the blood vessel thus snagged is greatly deformed, leading to turbulent sound which can be detected.

With the present embodiment, the turbulent sound can be detected by the small-vibration-detecting curving displacement sensor chip 75 formed of a high-polymer piezo bimorph sensor disposed near the needle portion 74 or the ceramic ball portion 73.

Thus, with the present embodiment, the detection signals are subjected to signal processing in order to detect the presence or absence of blood vessels, thereby notifying the surgeon of the presence or absence of the blood vessel.

While needle portion 74 has a function for stopping some bleeding due to coagulating actions by high-frequency heating, it is difficult to handle a large amount of bleeding. The mucous-tissue resection device according to the present embodiment has the advantage of preventing such a large amount of bleeding due to unintentional severing of blood vessels having a relatively large diameter.

Sixth Embodiment

Next, description will be made regarding a sixth embodiment according to the present invention with reference to FIG. 12.

The present embodiment relates to signal processing means and a signal processing method for improving an S/N ratio of turbulent sound signals, and may be applied to a sensor for detecting turbulent sound having any one of configurations described in the above embodiments.

For example, the present embodiment may be applied to any one of the pressing probe 5 including the bimorph sensor 8 formed of a high-polymer piezo device according to the first embodiment shown in FIG. 1B, the bimorph sensor 37 according to the second embodiment shown in FIG. 4, the bimorph sensor 40 shown in FIG. 6, the turbulent sound sensor 50 shown in FIG. 7, and the microphone 54 shown in FIG. 8.

The detection signals from any one of these turbulent sound sensors are detected over time, and more specifically, the detection signals are pulse signals which change over time. While the pulse signals contains noise signals due to beating of the heart, the pulse signals also contain noise signals occurring at random points in time.

Figure 12:
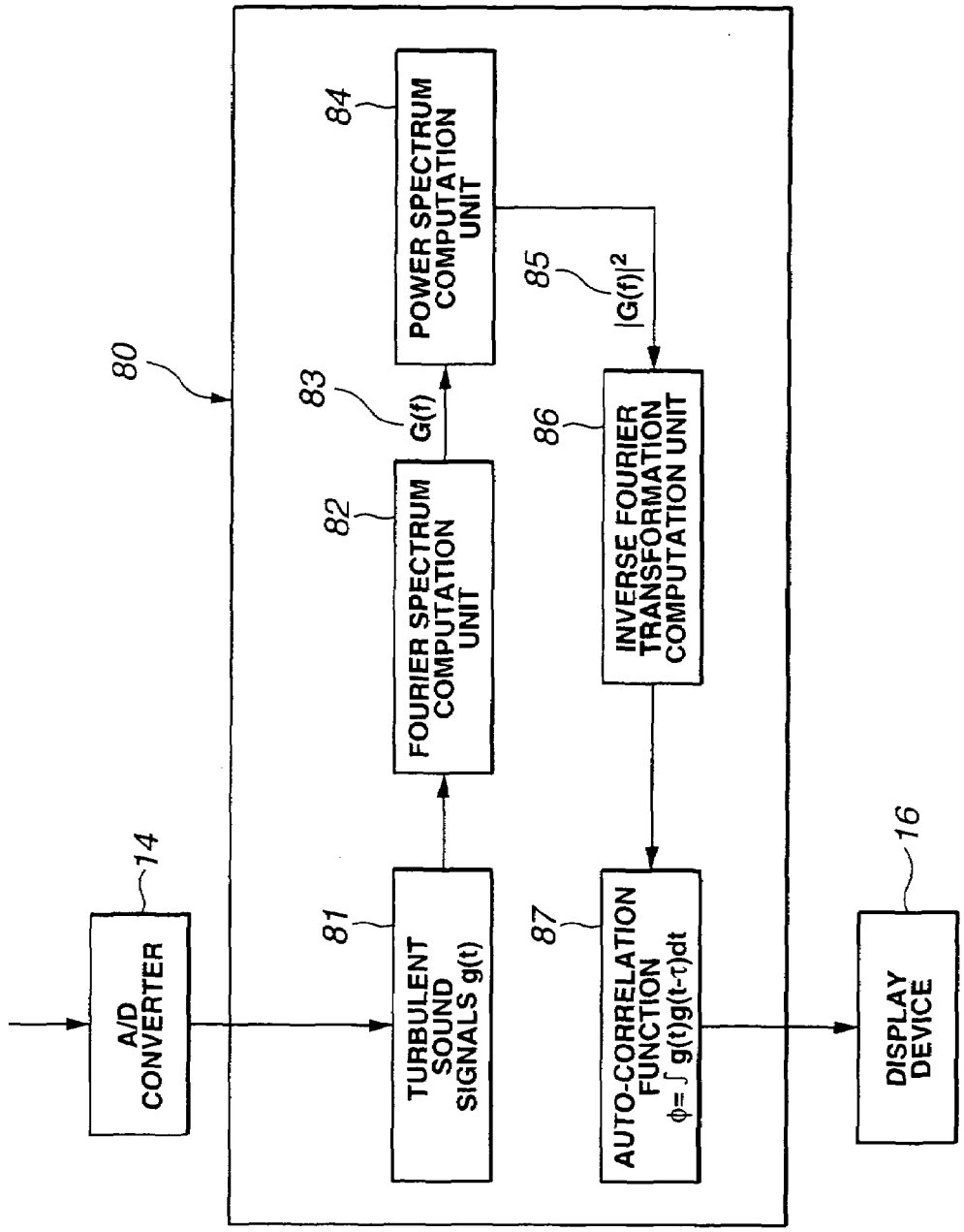
FIG. 12 is a block diagram which shows a configuration of the signal processing device according to a sixth embodiment of the present invention.

FIG. 12 shows a signal processing device 80 for removing such random noise. First, turbulent sound signals are converted into digital turbulent sound signals $g(t)$ 81 by the A/D converter 14. Subsequently, the digital turbulent sound signals $g(t)$ 81 are subjected to Fourier transformation by a Fourier spectrum computation unit 82, whereby the digital turbulent sound signals $g(t)$ 81 are converted into frequency characteristic components $G(f)$ 83.

Furthermore, the power spectrum computation unit 84 performs computation wherein the square of the absolute value of the frequency characteristic component $G(f)$ 83 is computed, whereby the power spectrum of the turbulent sound $|G(f)|^2$ 85 is generated. Furthermore, the power spectrum of the turbulent sound signals $|G(f)|^2$ 85 is subjected to inverse Fourier transformation by an inverse Fourier transformation computation unit 86, whereby the autocorrelation function $\phi 87$ is obtained.

The autocorrelation function $\phi 87$ is input to the display device 16, and the display device 16 notifies the surgeon of the presence or absence of blood vessels underneath mucous tissue based upon the autocorrelation function $\phi 87$.

The autocorrelation function $\phi 87$ represented by $\int g(t) g(t-\tau) dt$ is used for a computation algorithm for removing noise at a high speed, thereby enabling detection of turbulent sound with an excellent S/N ratio by performing the aforementioned series of computation processing. On the other hand, the most general method for removal of noise employs a bandwidth filter described in the first embodiment.

However, such a configuration needs to include computation means for computing the frequency property of the turbulent sound prior to filter processing. Furthermore, an arrangement may be made wherein detection signals are averaged in order to reduce noise, but such a configuration leads to increased computation period of time.

With the present embodiment shown in FIG. 12, detection of turbulent sound signals can be made with an excellent S/N ratio by a simple series of computation processing.

Note that the autocorrelation function $\phi 87$ is calculated by integration, and accordingly, the autocorrelation function $\phi 87$ may be computed by directly calculating the integration value. On the other hand, general-purpose programs using fast Fourier transformation (FFT) algorithm are available, and accordingly, an arrangement may be made wherein the autocorrelation function $\phi 87$ is computed using such a program, thereby enabling computation of the autocorrelation function $\phi 87$ with excellent reliability at high speed.

As described above, with such embodiments, blood vessels having a relatively large diameter extending underneath mucous tissue near malignant tumor tissue which is to be resected are greatly deformed in Endoscopic Mucosal Resection (EMR), and turbulent sound due to the deformation is detected with a high S/N ratio, thereby enabling determination of the presence or absence of blood vessels.

Thus, Endoscopic Mucosal Resection (EMR) can be effectively performed.

Note that all modifications formed of any combination of parts or the like of the above-described embodiments is encompassed by the present invention. For example, an arrangement may be made wherein the blood-vessel detecting probe 9 shown in FIG. 1B is inserted into the channel of the endoscope 42 shown in FIG. 7 (in this case, the suction cup 49 is not mounted onto the endoscope 42) so as to protrude from the forceps opening 48b formed on the tip thereof, and the surgeon diagnoses whether or not there are any blood vessels extending underneath the affected portion by observing the mucous tissue through the observation window 45.

Furthermore, an arrangement may be made wherein the high-frequency snare 33 is disposed so as to protrude from the other forceps opening 48a as shown in FIG. 7, so that the surgeon can presses the loop portion 33a in contact with the mucous tissue so as to surround the portion deformed by pressing force from the pressing rod 5 of the aforementioned blood-vessel detecting probe 9.

Note that the configurations disclosed in the present invention are not restricted to the medical application of EMR, rather, the configurations according to the present invention may be applied to any sort of medical applications of diagnosis for the body cavity using an endoscope, and have the advantage of preventing unintentional severing of blood vessels during operations of the treatment tool.

In particular, the devices and methods according to the present invention are effectively applied to medical treatment wherein blood vessels may generate turbulent sound due to great deformation thereof by operations of the treatment tool.

Furthermore, the devices and methods according to the present invention may be applied to medical treatment wherein, even if the surgeon cannot deform blood vessels, the endoscope can access near the affected portion, and blood vessels therearound generate turbulent sound due to blood vessel swelling or deposits accumulated therein.

Accordingly, the mucous-tissue resection device according to the present invention detects turbulent sound due to blood vessels extending underneath the aforementioned deformed part of the tissue within the body cavity, containing an affected portion or the like which is to be resected, thereby enabling detection of blood vessels underneath the tissue with simple operations.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A blood-vessel detection device for detecting the presence or absence of blood vessels underneath the tissue surface, the blood-vessel detection device comprising:
   a partially-deforming device having a cylindrical shape or a rod shape which is disposed or disposable onto the tip of an endoscope insertable into the body cavity so as to be in contact with the tissue surface in order to deform a part of the tissue surface, thereby generating turbulence in blood passing through blood vessels extending underneath the tissue surface;
   a converting device for converting turbulent sound due to the turbulence generated in a part of the tissue surface deformed by the partially-deforming device into electric signals; and
   a signal processing device for performing signal processing including at least amplification for the electric signals,
   wherein the partially-deforming device includes one of a resecting device for resecting the tissue which is to be resected, a binding device for binding a part of the tissue using a rope, and a suctioning device formed of a generally cylindrical cup.

2. The blood-vessel detection device according to claim 1, wherein the converting device and the partially-deforming device for deforming a part of the tissue surface integrally form a single unit.

3. The blood-vessel detection device according to claim 2, further comprising an endoscope including an inserting portion for being inserted into the body cavity, wherein the partially-deforming device is inserted into a channel of the endoscope or mounted onto the tip of the inserting portion.

4. The blood-vessel detection device according to claim 3, wherein the resecting device is further inserted in the channel of the endoscope for resecting tissue such as an affected portion or the like which is to be resected.

5. The blood-vessel detection device according to claim 3, wherein the partially-deforming device comprises a small-diameter rod which can be inserted into the channel or a cylindrical member which can be mounted onto the tip of the inserting portion.

6. The blood-vessel detection device according to claim 1, wherein the partially-deforming device comprises a pressing device formed of a small-diameter rod.

7. The blood-vessel detection device according to claim 6, wherein the small-diameter rod also has a function serving as a tissue-resecting device for resecting the tissue.

8. The blood-vessel detection device according to claim 7, wherein the tissue-resecting device comprises a needle knife.

9. The blood-vessel detection device according to claim 1, wherein the rope also has a function serving as a tissue-resecting device for resecting the tissue.

10. The blood-vessel detection device according to claim 9, wherein the tissue-resecting device comprises a high-frequency snare.

11. The blood-vessel detection device according to claim 1, wherein the cup also has a function serving as a tissue-resecting device for resecting the tissue.

12. The blood-vessel detection device according to claim 11, wherein the tissue-resecting device comprises a high-frequency snare integrally included within the cup.

13. The blood-vessel detection device according to claim 1, wherein the convening device comprises a sound-wave detecting device for detecting sound waves while being in contact with the tissue.

14. The blood-vessel detection device according to claim 13, wherein the sound-wave detecting device comprises a bimorph sensor using the piezo effect.

15. The blood-vessel detection device according to claim 14, wherein the bimorph sensor is formed of a high-polymer piezo device.

16. The blood-vessel detection device according to claim 1, wherein the converting device comprises a microphone serving as a non-contact-type wave-sound detector.

17. The blood-vessel detection device according to claim 16, wherein the microphone comprises a piezo bimorph microphone using the piezo effect, or an electrostatic microphone using the electrostatic effect.

18. The blood-vessel detection device according to claim 1, wherein the converting device is formed of a sound-interrupting unit for forming an acoustically isolated space with the part of the tissue surface as the bottom thereof and a microphone disposed therewithin.

19. The blood-vessel detection device according to claim 1, wherein the converting device includes a background noise sensor.

20. The blood-vessel detection device according to claim 19, wherein the background noise sensor is disposed within a space distanced from the space including the acoustic sensor during observation in the body cavity.

21. The blood-vessel detection device according to claim 19, wherein the signal processing device includes a differential output device for outputting differential signal between the electric signal and the output signal from the background noise sensor.

22. The blood-vessel detection device according to claim 1, wherein the signal processing device includes an amplifying device for amplifying electric signals, and a signal processing device for converting the electric signals into digital signals.

23. The blood-vessel detection device according to claim 22, wherein the signal processing device includes a Fourier transformation device, and a device for calculating after the Fourier transmission the mid-band frequency and the lower- and upper-side cutoff frequencies which are lower than that of the mid-band frequency by a predetermined decibel.

24. The blood-vessel detection device according to claim 23, wherein the signal processing device includes a digital filter device designed using data such as the mid-band frequency and the lower- and upper-side cutoff frequencies which are lower than that of the mid-band frequency by a predetermined decibel calculated by the device for calculating the data.

25. The blood-vessel detection device according to claim 22, wherein the signal processing device includes an autocorrelation-function computation device for computing the autocorrelation function of the electric signals.

26. The blood-vessel detection device according to claim 1, further comprising an endoscope including an inserting portion for being inserted into the body cavity wherein the partially-deforming device is inserted into a channel of the endoscope or mounted onto the tip of the inserting portion.

27. The blood-vessel detection device according to claim 26, wherein the resecting device is further inserted in the channel of the endoscope for resecting tissue such as an affected portion or the like which is to be resected.

28. The blood-vessel detection device according to claim 26, wherein the partially-deforming device comprises a small-diameter rod which can be inserted into the channel or a cylindrical member which is mounted onto the tip of the inserting portion.

* * * * *

UNITED STATES PATENT AND TRADEMARK OFFICE
CERTIFICATE OF CORRECTION

PATENT NO. : 7,488,292 B2
APPLICATION NO. : 10/872989
DATED : February 10, 2009
INVENTOR(S) : Hideo Adachi Page 1 of 1

It is certified that error appears in the above-identified patent and that said Letters Patent is hereby corrected as shown below:

Col. 19 Claim 13 line 8
"convening" should read -- converting --

Signed and Sealed this

Twenty-sixth Day of May, 2009

JOHN DOLL
*Acting Director of the United States Patent and Trademark Office*